United States Patent [19]

Capelle et al.

[11] 4,150,951

[45] Apr. 24, 1979

[54] MEASUREMENT OF CONCENTRATIONS OF GASEOUS PHASE ELEMENTS

[75] Inventors: Gene A. Capelle, Goleta; David G. Sutton, Huntington Beach; Sidney W. Benson, Palos Verdes Estates, all of Calif.

[73] Assignee: The Aerospace Corporation, El Segundo, Calif.

[21] Appl. No.: 834,224

[22] Filed: Sep. 19, 1977

[51] Int. Cl.² .................... G01N 21/26; G01N 21/38; G01N 27/64

[52] U.S. Cl. ........................... 23/232 E; 23/230 PC; 422/78; 422/98; 250/361 R; 250/459

[58] Field of Search ........ 23/230 PC, 253 PC, 232 E, 23/254 E, 230 R, 253 R; 250/361 CR, 458, 459

[56] References Cited

U.S. PATENT DOCUMENTS

| | | | |
|---|---|---|---|
| 3,713,773 | 1/1973 | Fontijn et al. | 23/232 E |
| 3,904,366 | 9/1975 | Grasenick | 23/230 PC |
| 3,926,562 | 12/1975 | Williams et al. | 23/230 PC |
| 3,963,928 | 6/1976 | Zolner | 23/254 E |
| 3,973,910 | 8/1976 | Fine | 23/230 R X |
| 3,977,831 | 8/1976 | Fletcher et al. | 23/230 R X |

OTHER PUBLICATIONS

Selective Laser Excitation of Charge Compensated Sites in $CaF_2:Er^{3+}$* Tallant et al., J. of Chem. Physics, vol. 63, No. 5, pp. 2074–2085.

Kinetics of Nitrogen Atom Recombination, Herron et al., J. of Chem. Physics, pp. 879–885; vol. 30, #4, 4—1959.

*Primary Examiner*—Morris O. Wolk
*Assistant Examiner*—Michael S. Marcus
*Attorney, Agent, or Firm*—Francis R. Reilly

[57] ABSTRACT

A method and apparatus for the quantitative and qualitative analysis of the elemental composition of materials in concentrations as low as a few atoms, or molecules, per cubic centimeter. When introduced into a gas stream containing an excess of an energetic metastable species of nitrogen or noble gas, the material, if atomic, is rapidly and repeatedly excited, or, if molecular, it is decomposed and subsequently certain component atoms of the molecule are excited, and thereupon fluoresce at their characteristic wavelength(s). The wavelength(s) and intensity of the emitted light (fluorescence) are determinative respectively of the identity and the concentration of the atoms of the different elements present.

6 Claims, 1 Drawing Figure

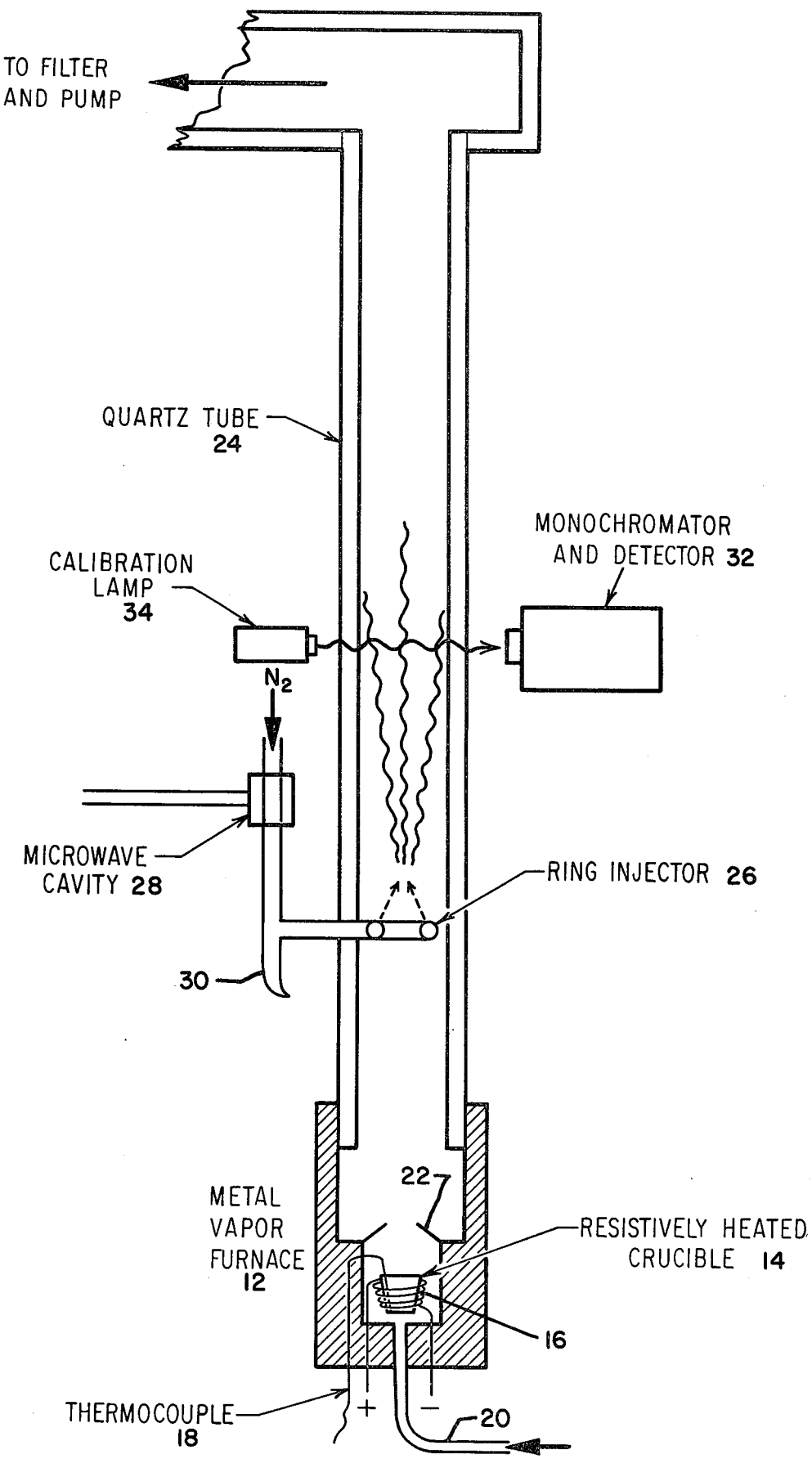

MEASUREMENT OF CONCENTRATIONS OF GASEOUS PHASE ELEMENTS

BACKGROUND OF THE INVENTION

1. Field of the Invention

The present invention is directed to the qualitative and quantitative analysis of elements in a sample when present in medium to ultra-low concentrations, by measurement of the wavelength and intensity of their fluorescence when the sample is introduced as a vapor in a gas stream containing an excess of energetic metastable species of nitrogen or an inert gas.

2. Description of the Prior Art

There is an abundance of literature and many varieties of apparatus in the field of the analysis of the elements and their compounds. Two of the most widely used techniques are atomic and molecular emission spectrometry and atomic absorption spectrometry. These techniques are generally recognized to have lower limits of sensitivity and accuracy to concentrations of $10^8$ atoms per cubic centimeter ($cm^3$). Particularly with the advent of lasers, atomic fluorescence spectrometry has been improved to provide sensitivities to less than several hundred atoms per $cm^3$ with some experimenters reporting the detection of a single atom. Under laser excitation at a wavelength within the absorption spectrum of the atomic species under study the measurement of the resulting atomic fluorescence has emerged as one of the most sensitive techniques in spectroscopy. This sensitivity is provided by the atomic species under laser illumination participating repeatedly in the almost simultaneous excitation-emission process whereby a plurality of signals is produced by each atom. Unfortunately there are wavelength limitations on methods employing laser excitation. The principal limitation is that any single laser cannot normally be used to excite several different atomic species simultaneously, and certain species cannot at all be analyzed because of the unavailability of a laser with the required absorption-matching wavelength. Other disadvantages of using laser excitation are the expense of sophisticated lasers and, in some cases, the capability of certain lasers to operate only in a pulsed mode, thus reducing the sensitivity of the method.

The present invention employs an active metastable species of a gas, such as nitrogen or the inert gases, to excite atomic species, particularly, but not limited to, the metallic elements, to fluorescence. The active metastable is also capable of dissociating compounds and subsequently exciting the resulting constituent atoms. This phenomenon is generally reported in the literature. One of the most pertinent discussions of the fluorescent emissions of certain metals by collision with active nitrogen is offered by L. F. Phillips, *Canadian Journal of Chemistry,* Volume 41 (1963) 2060-2066. Phillips, as well as other researchers, recognize generally that the fluorescent emission of the metallic atoms in the presence of active nitrogen varies in intensity in some ratio to the concentration of the metal. In all known reported works, it is particularly noteworthy, however, that only high concentrations of additives were employed in the experiments and the experimenters were not concerned with precise quantitative analysis of the fluorescing atoms or their compounds. Moreover, it is apparent from such as the Phillips report that the phenomenon of fluorescence of atoms by active nitrogen excitation was not accurately or completely understood, and for this reason prior researchers failed to recognize its application to the quantitative and qualitative analysis, especially of ultra-low concentrations of elements.

Phillips' reported work was limited primarily to the excitation of metal halides by active nitrogen. He explains that in a one-step reaction the metal halide is dissociated by active nitrogen, producing the halogen and the metal in an excited state, with the metal fluorescing at its characteristic wavelength. From his experiments and observations Phillips concludes that thallium and lead atoms are not excited to any significant degree by active nitrogen, but rather that the metals are efficiently excited to fluoresce only upon dissociation from a molecular state. Thus, the theory of the simultaneous activation-dissociation-fluorescence sequence as deduced by Phillips concluded that each molecule of the metallic compounds (e.g., thallium halide) fluoresces only once. Thereafter, the dissociated metal atoms were observed by Phillips not to be reactivated to fluorescence. In this connection it must be realized that Phillips' analysis was based on his observations of the experiment as actually performed.

The prior art has overlooked the use of active-nitrogen-induced fluorescense of atoms to detect extremely low concentrations thereof. In fact, some workers in the prior art, such as Phillips (discussed above) have concluded that the process is not an effective analytic tool for high concentrations of atomic species. Perhaps because of this conclusion, no prior attempt was directed to its application to the analysis of very low concentrations in the vapor phase. We surmise the prior art may have been directed away from our invention because previous apparatus for this process may have been constructed in such a manner as to disperse the material ineffectively into the gas flow containing the active nitrogen or was otherwise not properly tailored for the purpose of our invention. Also, since at high concentrations of sample material the active species can be quenched, thus producing only a very low rate of excitation, it might have been erroneously concluded that such rate would not produce a meaningful intensity of fluorescense at low concentrations.

SUMMARY OF THE INVENTION

Our present invention is based on the discovery that low concentrations of atoms of various elements, when dispersed in an excess of active nitrogen or energetic metastable noble gas molecules, are each repeatedly and rapidly excited to fluoresce. The intensities of the fluorescence are not merely an indication of the relative concentrations of the atoms, but rather are direct, substantially linear functions of the number of atoms present, with the lowest theoretical level of detection attainable being a single atom. Our invention does not extend to regions of high concentrations of atoms ($\geq 10^{13}$ atoms/$cm^3$) in active nitrogen (or excited noble gases) where there ceases to be an extremely high ratio of the active gas to sample atoms. Under this latter condition, the fluorescent emissions per unit time by the atoms saturate as a result of the depletion of the concentration of active species due to bimolecular collision with the sample species. When the concentration of atoms attains a ratio to the active gas high enough to decrease significantly the concentration of the active species, the intensity of the fluorescence is then no longer a simple linear function of the concentration of the sample atoms.

The general assembly of the apparatus here employed has many features in common with prior apparatus but is characterized by several critical distinct components required to enable it to perform the analytical work embodied in our invention.

Our apparatus includes a source of the sample under analysis, with the material being in or converted to its gaseous phase. The sample may initially be in the solid, liquid or gas phase. It may initially exist as an element, alloy, solution, composition form, or in a gaseous dispersion as an exhaust gas or in the atmosphere. Normally the vaporized sample species will be mixed with and entrained in a flow of carrier gas and conveyed into a flow-type fluorescence cell. Conditioning of the carrier gas, such as by heating or cooling, may compose an integral part of the sample preparation in some cases. The region in which the mixing is accomplished is configured to assure that the sample vapor has the minimal opportunity to impinge on any exposed walls of the apparatus that would result in its removal from the stream via adherence to the walls. Immediately downstream of the sample injection point in the flow cell, a flow of active metastable nitrogen or noble gas is introduced and mixed with combined flow of sample vapor and carrier gas so as to result in the sample vapor being dispersed throughout the active nitrogen. This dispersion is accomplished by injecting the active nitrogen in the form of one or more strategically placed and directed streams.

Upon mixing of the sample vapor with the active nitrogen, biomolecular collisions of sample particles with active nitrogen species serve to excite the sample to fluoresce. Various compounds can be dissociated and their constituents excited by the same process. The ratio of concentrations of the active nitrogen to the vapor phase sample is very high to assure that the active nitrogen is not depleted during the time span in which measurements are made of the fluorescent emissions.

At a fixed distance (long enough to insure mixing and short enough to avoid significant sample loss) downstream of the injection point of the active nitrogen, the fluorescence is monitored to determine the wavelengths and corresponding intensities to establish, respectively, the identity of the one or more elements present and their respective concentrations in the flowing stream. Alternatively, the fluorescence can be monitored solely to determine the presence or absence of a specific wavelength(s) characteristic of a given element, and, if present, the intensity will be indicative of its concentration. The calibration of the fluorescence intensities in terms of atoms per unit volume is established by known techniques. In addition, the invention can be readily constructed to provide for the following capabilities. Multiple element samples may be analyzed for several constituents simultaneously. Detection of rarified beams by this technique is possible. The technique may be utilized to provide real time analysis of sample flows such as emission gases. Molecular samples can readily be analyzed in terms of their atomic constituents, either directly by dissociative energy transfer or with the application of additional heating, electric discharge or other energy transfer techniques to the sample. Laser blow-off as well as conventional pyrolytic techniques may be used to prepare refractory samples for analysis. Various standard sample handling devices can be adapted for use in this apparatus. These include but are not limited to spark and arc sources, nebulizers and evaporators.

DESCRIPTION OF THE DRAWING

FIG. 1 is a partially schematic, partially sectional side view of one configuration of the apparatus for measuring ultra-low concentrations of vaporized species in a carrier gas in accordance with the present invention.

DESCRIPTION OF THE INVENTION

One presently preferred form of apparatus constituting our invention and capable of carrying the method of our invention is shown in FIG. 1. It includes an evaporative source for injecting solid samples into the vapor state, where they are subject to analysis. This source, in the form shown, is a metal vapor furnace 12 comprising a ceramic crucible 14 heated by an electrical resistance coil 16. The material is loaded into the crucible 14 to be heated to a temperature effecting its partial vaporization. The temperature of the material is sensed by thermocouple 18 in contact with the material in crucible 14. The vapor driven off is entrained in a flow of carrier gas entering via duct 20 to flow about and over the top of crucible 14. The carrier gas is selected from those gases that do not extract energy from or deplete active metastable species, such carrier gases being typically one of the inert gases, nitrogen or hydrogen. The vapor entrained in carrier gas exits furnace 12 via constrictor 22 which is appropriately configured to direct the flow in order to minimize vapor impingement on the interior surfaces of the furnace 12. This precaution is taken to prevent the loss of vapor by condensation on and adherence to the surfaces.

After exiting the furnace 12 the combined carrier gas and vapor stream enters a flow type cell comprising a quartz tube 24 having its interior evacuated by a vacuum pump (not shown) connected to the upper end of tube 24. At the lower end of tube 24, active metastable nitrogen, or an active metastable noble gas, is injected into the tube 24 to mix with the entrained gas phase material. As used herein the terms "active metastable nitrogen" and "active nitrogen" are to be considered to include also the active noble gases. In the form of apparatus shown, the active nitrogen is injected upwardly into tube 24 from an annular or ring injector 26 through a plurality of circumferentially spaced ports. Active nitrogen is generated by passing ground state nitrogen ($N_2$) through the cavity of a microwave generator 28, then introduced through ducting 30 to ring injector 26. Various alternate discharge, electron impact or energy transfer techniques may also be employed to prepare active nitrogen or metastable rare gas species. The ring injector 26, or other alternate configuration, provides a laminar or turbulent flow (depending on the pressure) of active nitrogen merging with the entrained vaporous material from furnace 12 serving to disperse the active nitrogen within the flow of vaporous material. With the vacuum pump in operation and the active nitrogen, carrier gas and vaporized material flowing in the cell, the total internal pressure will normally be in the range of 0.5 to 10.0 Torr or higher.

Active nitrogen consists in large part of electronically excited $N_2(A^3\Sigma^+_u)$ molecules which are metastable or long-lived to an extent up to 10 milliseconds or greater. On collision of active nitrogen with sample atoms in the vapor, energy is transferred, reducing the nitrogen molecule impacted to a lower energy level or its ground state and producing excitation of the atom, with the subsequent fluorescence of the atom at its characteristic wavelength(s). Various types of compounds can be dissociated by this process, and subsequently the resulting atomic constituents are collisionally excited to fluoresce. The essence of the present invention resides in the supply of an "excess" or very high ratio of active nitrogen molecules to sample atoms so that the collisional energy transfer-fluorescence cycle can occur repeatedly (yielding many photons per sample atom) without depleting the active nitrogen concentration.

The intensities of the fluorescent sample emissions and their respective wavelengths are measured at a distance immediately downstream from the ring injector 26. This distance is long enough to provide for adequate mixing of the active nitrogen and sample bearing flows while short enough so that losses of the active nitrogen due to collisional or wall quenching are not significant. These measurements are made with conventional monochromator (or other wavelength selective device) and detector shown schematically at 32. In the apparatus as shown, a calibration lamp 34 is also included to provide a reference base by which the detector output signals are converted to units of sample atom concentrations.

The sensitivity of the apparatus may be calibrated by injecting into the active nitrogen flow samples of vapors of known concentrations. Standard atomic abosrption techniques will serve to calibrate the detector output at concentrations ranging down to $10^9$ atoms per cubic centimeter. This calibration can be extrapolated to the lower concentrations by the use of the Clausius-Clapeyron equation for materials with well defined vapor pressure curves. In fact this method can be used to determine the vapor pressure curves of samples, and thereby obtain heats of vaporization or sublimation.

In one form as actually constructed, the quartz flow tube employed had an internal diameter of 9 centimeters. The vacuum pump attached to the top of the quartz tube had a capacity of 60 liters per second. A charge of bismuth was placed in the crucible 14 and its temperature was elevated by the heater coil 16. Argon was injected as the Bi vapor carrier gas at a concentration of approximately $10^{16}$ atoms per cubic centimeter. Nitrogen was supplied to the microwave cavity 28 operating at a power of 70 watts. About 5 centimeters downstream from ring injector 26, the flow in the cell 24 was monitored photoelectrically with an RCA 1P28 phototube attached to a ½ meter monochromator. A hollow cathode Bi lamp was placed on the opposite side of the flow tube and at the same height as the monochromator entrance slits. It was used as a line source for the atomic absorption measurements to calibrate the fluorescence intensity measurements with respect to Bi vapor concentration.

The Ar and $N_2$ flows ($10^{21}$/sec and $2\times10^{20}$/sec, respectively) were adjusted to give a total pressure of 0.5 Torr. With the microwave generator set to deliver 70 Watts to the $N_2$ flow, a pale straw-colored glow was observable downstream of the injector. The furnace was then set to temperature T and the resulting atomic Bi emission was measured. This consisted predominantly of the 3068 A line. The log of the intensity of the 3068 A line at several temperatures was plotted against $10^4/T(°K)$. The slope of the resulting straight line is the same as a plot (suggested from a critical review of the literature) of the log of the Bi equilibrium vapor pressure versus $10^4/T(°K)$. The fluorescence intensity from the excited Bi in the obseration zone was thus observed to be proportional to the equilibrium vapor pressure of ground-state metal at the furnace temperature. Similar plots were made from the log of the intensity data of eight different Bi emission lines, and all were linear with the same slope over the temperature range in which they could be observed.

At the higher temperatures, the Bi density was sufficient to make atomic absorption measurements by means of the 3068 A line from the Bi hollow cathode lamp, thereby directly determining the Bi atom ground state concentration. The results for several values of the source temperature were also plotted. These points and the known slope for the log of the Bi concentration vs 1/T curve established a calibrated scale for equating the fluorescence intensity to Bi concentration down to less than $10^4$ atoms per cubic centimeter of Bi. The range of sensitivity is projected to be extendable to concentrations of 100 atoms per cubic centimeter, or less, for Bi and other atoms which fluoresce in the presence of active nitrogen.

A variety of methods including the evaporative system described above can be employed as internal standards to inject a known concentration of sample material into the gas stream. The fluorescence intensity from the internal standard and the intensity of the intrinsic fluorescence from the energetic metastable species may be used in conjunction with an experimentally determined master matrix of sensitivities to calibrate any device and for meaningful comparisons between different devices.

Because of its extremely high sensitivity and relative simplicity, the method described here has numerous immediate applications and many more potential applications. It should be relatively easy to measure vapor pressure curves accurately for most of the elements over a range of more than eight orders of magnitude. Real time analysis is practical. The method offers a reasonably simple means of monitoring and analyzing exhaust and stack emissions. Other possible applications include solid state device analysis (for trace impurities), forensic analysis, e.g., of hair or explosives, and nondestructive material and alloy analysis.

We claim:

1. The method of quantitative and qualitative analysis of ultralow concentrations of an element in its gaseous phase with the lower limit of the range of concentrations approaching several atoms per cubic centimeter comprising:
    (a) flowing a confined stream of an active metastable gaseous species selected from the group consisting of nitrogen and the noble gases;
    (b) diffusely merging a flow of the gaseous phase element with the stream of the active metastable species to effect the widest dispersion of the gaseous phase element in the active metastable species;
    (c) colliding said active metastable gaseous species with the gaseous phase element—thereby generating fluorescence;
    (d) maintaining the ratio of the concentrations of the metastable gaseous species to the gaseous phase element high enough to preclude, within the observation zone, the depletion of the concentration of the active metastable species; and
    (e) measuring the intensity and the one or more wavelengths of fluorescence whereby to provide the identity of the element and its concentration.

2. Apparatus for quantitative and qualitative analysis of a sample containing one or more metallic or metal-like elements in concentrations having a lower limit of several atoms per cubic centimeter, each of said elements being excitable to fluorescence at its one or more characteristic wavelengths by collision with an energetic metastable gaseous species, comprising:
  (a) a flow-type fluorescence cell;
  (b) means for supplying the sample in the gas phase and flowing the sample into and through the cell;
  (c) source-means of a metastable active gaseous species;
  (d) means for injecting an excess of the energetic active gaseous species into the cell and effecting a rapid and uniform dispersion of the gaseous phase sample throughout the energetic gaseous species, thereby promoting fluorescence by collisions between the sample and the energetic gaseous species;
  (e) sensing means illuminated by the fluorescence, said sensing means determining the presence of each of the one or more the characteristic wavelengths of the fluorescence, said sensing means further measuring the intensity of the fluorescence at each of said wavelengths and being calibrated to indicate concentrations in the range of $1-10^{12}$ atoms per cc fluorescing at the measured wavelengths.

3. Apparatus as defined in claim 2 and further including means to control the total pressure within the fluorescence cell to approximately 0.5 to 10 torr.

4. Apparatus as defined in claim 2 wherein the sensing means are located in the apparatus downstream from the mixing region of the gas phase sample material and the metastable gaseous species at a distance providing uniform dispersion of the gaseous sample substance in the metastable species with minimal loss of the sample on the walls of the cell prior to reaching the sensing means, said distance being approximately equal to the width or diameter of the flow-type cell.

5. Apparatus as defined in claim 2 wherein the species in its energetic metastable state is active nitrogen.

6. Apparatus is defined in claim 2 wherein the energetic metastable species is selected from the group consisting of the noble gases and nitrogen.

* * * * *